(12) United States Patent
Sato et al.

(10) Patent No.: US 7,193,110 B2
(45) Date of Patent: Mar. 20, 2007

(54) METHOD FOR PRODUCING CARBOXYLIC ACID

(75) Inventors: Kazuhiko Sato, Ibaraki (JP); Yoko Usui, Ibaraki (JP)

(73) Assignee: National Institute of Advanced Industrial Science and Technology, Tokyo (JP)

( * ) Notice: Subject to any disclaimer, the term of this patent is extended or adjusted under 35 U.S.C. 154(b) by 42 days.

(21) Appl. No.: 10/539,209

(22) PCT Filed: Nov. 12, 2003

(86) PCT No.: PCT/JP03/14360

§ 371 (c)(1),
(2), (4) Date: Jun. 17, 2005

(87) PCT Pub. No.: WO2004/054956

PCT Pub. Date: Jul. 1, 2004

(65) Prior Publication Data

US 2006/0167311 A1 Jul. 27, 2006

(30) Foreign Application Priority Data

Dec. 18, 2002 (JP) .............................. 2002-365964

(51) Int. Cl.
*C07C 51/16* (2006.01)

(52) U.S. Cl. ...................................... 562/531; 562/418

(58) Field of Classification Search ................ 562/531, 562/418
See application file for complete search history.

(56) References Cited

U.S. PATENT DOCUMENTS

| 4,093,649 | A | * | 6/1978 | Kao et al. | .................... 562/533 |
| 4,549,025 | A | * | 10/1985 | Dalcanale et al. | .......... 546/327 |
| 5,801,276 | A | | 9/1998 | Neumann et al. | |

FOREIGN PATENT DOCUMENTS

| DE | 196 32 922 | 2/1998 |
| EP | 21525 | 1/1981 |
| EP | 0320346 | 6/1989 |
| JP | 48-417 | 1/1973 |
| JP | 61-118343 | 6/1986 |
| JP | 2003-12633 | 1/2003 |

* cited by examiner

*Primary Examiner*—J. Parsa
(74) *Attorney, Agent, or Firm*—Morgan, Lewis & Bockius LLP

(57) ABSTRACT

An aldehyde-containing oily solution and an aqueous hydrogen peroxide solution are reacted in the presence of a catalyst comprising a polymer compound having a sulfonic acid group in a side chain thereof in a heterogeneous solution system. According to such a reaction process, carboxylic acid can be efficiently produced under mild conditions having very little influence and toxicity on the environment and a human body, with simple operations, without requiring the operation for removing a solvent after the completion of the reaction.

3 Claims, No Drawings

METHOD FOR PRODUCING CARBOXYLIC ACID

TECHNICAL FIELD

The present invention relates to a process for producing carboxylic acid which is an important intermediate in the synthesis of diesters, polyesters and polyamides which are useful substances to be widely utilized in various industrial fields including chemical industries as plasticizers, lubricants, heat transfer media, dielectric media, fibers, copolymers, coating resins, surfactants, fungicides, insecticides, adhesives, and the like. More specifically, the present invention relates to a process for producing carboxylic acid by the reaction of aldehyde-containing oily solution with an aqueous hydrogen peroxide solution.

BACKGROUND ART

As processes for producing carboxylic acid by oxidizing aldehyde, reactions using potassium permanganate, manganese dioxide or silver oxide as an oxidizing agent are known. However, these processes load a large burden on the environment in view of the generation of highly toxic by-products, the corrosiveness of the oxidizing agents, and the like, so that it is hard to say that they are industrially excellent processes.

On the other hand, oxygen and hydrogen peroxide are inexpensive and non-corrosive, and no by-product is formed or a by-product is harmless water after the reactions, so that an environmental burden is small and thus it can be said that they are excellent oxidizing agents for industrial utilization.

Although processes for forming carboxylic acid from aldehyde using oxygen as an oxidizing agent is known (Non-Patent Document 1), in these processes, an acid, a base, or benzene is used as a solvent in the presence of a heavy metal catalyst such as silver or copper. Moreover, it is also reported that an oxidation reaction of aldehyde with oxygen catalyzed by nickel complex proceeds under mild conditions (Non-Patent Document 2), but it is necessary to use cyclohexanone, acetone, or the like as a solvent.

On the other hand, as processes for producing carboxylic acid from aldehyde using hydrogen peroxide as an oxidizing agent, there are known a process of using an equivalent amount of hexafluoroacetone in a methylene chloride solvent (Non-Patent Document 3) and a process of using formic acid as a solvent (Non-Patent Document 4).

Moreover, as processes for producing carboxylic acid utilizing catalytic oxidation reactions using hydrogen peroxide as an oxidizing agent, there are reported a process of forming a methyl ester using 28% of a sulfuric acid catalyst in a methanol solvent (Non-Patent Document 5), a process of using 5% of a PhSeOOH catalyst in a THF solvent (Non-Patent Document 6), a process of using a catalytic amount (0.9%) of HBr using dioxane as a solvent (Non-Patent Document 7), and a process of using 5% of an $SeO_2$ catalyst in a THF solvent (Non-Patent Document 8). In all these reactions, a water-soluble solvent which forms a homogeneous phase with an aqueous hydrogen peroxide solution, such as formic acid, methanol, THF or dioxane, is used as a solvent.

Thus, in the oxidation reactions of a water-insoluble aldehyde, the use of polar organic solvents as mentioned above is indispensable in order to form a homogeneous solution by dissolving a water-insoluble aldehyde in an aqueous hydrogen peroxide solution. As a result, at the isolation of carboxylic acid which is an objective product, a means for removing the polar organic solvents is necessary and reaction operations and apparatus become complex. Furthermore, the influence and toxicity of the organic solvents themselves on the environment and a human body have been pointed out.

Non-Patent Document 1: *Ind. Eng. Chem.*, 42 768–776 (1950)

Non-Patent Document 2: *Chem. Lett.*, 5–8 (1991)

Non-Patent Document 3: *Tetrahedron Lett.*, 21, 685–688 (1980)

Non-Patent Document 4: *Synthesis*, 21, 295–297 (1993)

Non-Patent Document 5: *J. Org. Chem.*, 49, 4740–4741 (1984)

Non-Patent Document 6: *Tetrahedron Lett.*, 29, 1967–1970 (1988)

Non-Patent Document 7: Specification of European Patent No. 424,242

Non-Patent Document 8: *Synth. Commun.*, 30, 4425–4434 (2000)

DISCLOSURE OF THE INVENTION

The present invention has been performed for overcoming the above problems of the conventional technologies, and an object thereof is to provide a safe, simple and efficient process for producing carboxylic acid by the reaction of aldehyde with an aqueous hydrogen peroxide solution, which enables the production of the carboxylic acid in high yields under mild reaction conditions as well as which dose not require the operation for removing a solvent after the completion of the reaction with simple reaction operations and is very little in influence and toxicity on the environment and a human body.

As a result of the extensive studies for solving the above problems, the present inventors have found that, instead of the conventional reaction process of carrying out an oxidation reaction in a homogeneous solution system of a non-aqueous aldehyde solution and an aqueous hydrogen peroxide solution in a polar organic solvent, the selection of the reaction using an heterogeneous solution system of an aqueous hydrogen peroxide solution and a water-insoluble aldehyde-containing oily solution in the presence of a polymer sulfonic acid catalyst enables the safe and simple production of the corresponding carboxylic acid in high yields, unlike the conventional common technical findings. Thus, they have accomplished the present invention.

Namely, the present invention provides the followings:

(1) A process for producing carboxylic acid, which comprises reacting aldehyde-containing oily solution with an aqueous hydrogen peroxide solution in the presence of a catalyst comprising a polymer compound having a sulfonic acid group in a side chain thereof in a heterogeneous solution system.

(2) The process for producing carboxylic acid according to the above (1), wherein the polymer compound is at least one polymer selected from a styrene polymer, a copolymer of styrene and divinylbenzene, and a fluorocarbon polymer.

(3) The process for producing carboxylic acid according to the above (1) or (2), wherein the aldehyde is a compound represented by the following formula (1):

$$RCHO \qquad (1)$$

wherein R represents a monovalent group selected from hydrogen, an alkyl group, a cycloalkyl group, an aryl group, and an aralkyl group.

BEST MODE FOR CARRYING OUT THE INVENTION

The process for producing carboxylic acid by the oxidation reaction of aldehyde using hydrogen peroxide according to the present invention is characterized in that the oxidation reaction is carried out in a heterogonous solution of an aqueous hydrogen peroxide solution and aldehyde-containing oily solution in the presence of a catalyst comprising a polymer compound having a sulfonic acid group in a side chain thereof.

Hitherto, in a liquid-liquid reaction, when starting materials themselves or a starting material and reaction reagents such as an oxidizing agent and a reaction accelerator have no compatibility with each other, it is advantageous in view of the selectivity, yield and the like to use a process of preparing a homogeneous solution of both substances beforehand using a solvent in which the starting material(s) and the reaction reagent(s) mutually dissolve for smooth progress of the reaction and subsequently reacting them.

Even in the reaction of synthesizing carboxylic acid by the reaction of aldehyde with hydrogen peroxide, as mentioned above, following this concept, there has been adopted a process for producing carboxylic acid by reacting a homogeneous solution of a water-insoluble aldehyde and hydrogen peroxide using a polar solvent in the presence of an acid catalyst.

As a result of seeking various studies, experiments and theoretical consideration on such an oxidation reaction from the viewpoint of more efficient protection of the environment and a human body, the present inventors have found that the yield of the carboxylic acid is remarkably improved and also a remarkable contribution to the reduction of an environmental burden is achieved when the oxidation reaction of aldehyde using hydrogen peroxide as an oxidizing agent is carried out not in a homogeneous solution system, but in a heterogeneous solution system of the aldehyde-containing oily solution and the aqueous hydrogen peroxide solution unlike the conventional technical common knowledge and in the presence of a catalyst comprising a polymer compound having a sulfonic acid group in a side chain thereof. Such a finding cannot be expected based on the conventional common technical knowledge, but is a specific phenomenon which is first found as a result of accumulated sedulous experiments and studies by the inventors.

As the starting material for use in the process of the present invention, a hitherto known common aldehyde can be used and the material is not particularly limited, but the aldehyde represented by the following formula (1) is preferably used.

RCHO      (1)

wherein R has the same meaning as described above.

When R is an alkyl group, the number of the carbon atoms of the alkyl group is from 3 to 22, preferably from 5 to 18. Examples of the alkyl group include an octyl group, a 2-ethylhexyl group, and the like. When R is a cycloalkyl group, the number of the carbon atoms of the cycloalkyl group is from 5 to 12, preferably from 5 to 8. Examples of the cycloalkyl group include a cyclohexyl group, a cyclooctyl group, and the like. When R is an aryl group, the number of the carbon atoms of the aryl group is from 6 to 14, preferably from 6 to 10. Examples of the aryl group include a phenyl group, a naphthyl group, and the like. When R is an aralkyl group, the number of the carbon atoms of the aralkyl group is from 7 to 15, preferably from 7 to 11. Examples of the aralkyl group include a benzyl group, a phenethyl group, a naphthylmethyl group, and the like. Even when R is any of an alkyl group, a cycloalkyl group, an aryl group and an aralkyl group, the alkyl group, cycloalkyl group, aryl group and aralkyl group may be further substituted with a substituent(s) such as a hydrocarbon group, an alkoxy group, an aryloxy group, a cyano alkyl, a trimethylsilyl group or a hydroxy group. Moreover, when a formyl group and an olefin coexist in a molecule, olefincarboxylic acid obtained by selective oxidation of the formyl group is obtained.

Examples of the aldehyde to be preferably used in the present invention include octyl aldehyde, 3-phenylpropionaldehyde, 2-ethylhexyl aldehyde, trimethylacetaldehyde, 2-phenylpropionaldehyde, bezaldehyde, p-tolualdehyde, p-anisaldehyde, 10-undecenaldehyde, and the like.

In the present invention, as mentioned above, since it is an object to provide a safe, simple and efficient process for producing carboxylic acid from aldehyde by the reaction of the aldehyde with an aqueous hydrogen peroxide solution, which enables the production of the carboxylic acid from the aldehyde in high yields under mild reaction conditions as well as which dose not require the operation for removing a solvent after the completion of the reaction with simple reaction operations and is very little in influence and toxicity on the environment and a human body, an oily solution of the aldehyde itself and also an oily solution of the aldehyde dissolved in a non-polar solvent such as hydrocarbon which is not compatible with water may be mentioned as the aldehyde-containing oily solution. However, in view of the above reduction of environmental burden and the operation for removing the solvent, it is most preferable to use a water-insoluble aldehyde itself.

The oxidizing agent for use in the process of the present invention is hydrogen peroxide, which is used in an aqueous solution thereof at the application. The concentration of the aqueous hydrogen peroxide solution is not particularly limited since the oxidation reaction of the aldehyde occurs according to the concentration, but the concentration is generally selected from the range of 1 to 80% by weight, preferably 30 to 60% by weight.

Moreover, the amount of the aqueous hydrogen peroxide to be used is also not particularly limited, but is generally selected from the range of 1.0 to 10.0 equivalents, preferably 1.0 to 1.2 equivalents, to the aldehyde.

The catalyst for use in the process of the present invention is a catalyst mainly comprising a polymer compound having a sulfonic acid group in a side chain thereof. The reaction of the present invention is remarkably accelerated by using, as such a catalyst, a polymer compound wherein a sulfonic acid group is bound to a side chain thereof.

The polymer compound wherein a sulfonic acid group is bound to a side chain thereof exhibits the effect as a catalyst even when the polymer part has any structure, but a polymer compound which is insoluble in water and an organic substance, for example, a styrene polymer, a copolymer of styrene and divinylbenzene, or a fluorocarbon polymer wherein a sulfonic acid group is bound to a side chain thereof is preferably used. Examples of the polymer compound wherein a sulfonic acid group is bound to a side chain thereof include commercially available polymer compounds, such as Daiaion PK228 (manufactured by Mitsubishi Chemical Corporation) as a styrene polymer, Amberlyst 15 (manufactured by Organo Corporation) and MSC-1 (manufactured by Muromachi Technos Co., Ltd.) as styrene-divinylbenzene copolymers, and Nafion NR50 (manufactured by Du Pont) and Nafion SAC13 (manufactured by Du Pont) as fluorocarbon resins.

With regard to the amount of the polymer compound wherein a sulfonic acid group is bound to a side chain thereof to be used as a catalyst, since the reaction is accelerated as the amount increases, the sulfonic acid group can be used in large excess as the equivalent ratio of the sulfonic acid group to the formyl group of the aldehyde. However, although it depends on the reaction temperature, even when the equivalent ratio of the sulfonic acid group to the formyl group is 0.0001 to 0.2 equivalent, preferably 0.01 to 0.1 equivalent, it is possible to achieve a high yield within a relatively short time.

The catalyst for use in the production process of the present invention is mainly comprising the above polymer compound wherein a sulfonic acid group is bound to a side chain thereof, but, if necessary, it is also possible to use an auxiliary catalyst such as acetic acid, phosphoric acid, phosphate, sulfate, hydrogen sulfate or ammonium salt.

The reaction conditions of the process of the present invention are not particularly limited, but the reaction is usually carried out at the range of 30 to 120° C., preferably 50 to 100° C. The reaction pressure may be any of normal pressure, elevated pressure, and reduced pressure, but it is preferably carried out under normal pressure.

Moreover, in the production process of the present invention, the order of the addition of the starting material, the oxidizing agent, and the catalyst and the reaction mode are not particularly limited as far as they comprise a process wherein the aqueous hydrogen peroxide solution and the aldehyde form a heterogeneous solution in the reaction system. Usually, there is adopted a process wherein the aldehyde is added to the aqueous hydrogen peroxide solution mixed with the catalyst to form a heterogeneous mixture of the three substances beforehand and then they are reacted with stirring.

In the production process of the present invention, by adopting the above specific oxidation reaction process, from the aldehyde represented by formula (1), carboxylic acid such as a corresponding acid:

$$RCO_2H \qquad (2)$$

wherein R has the same meaning as described above, can be obtained in a high yield.

Examples of the carboxylic acid to be obtained by the process of the present invention include octanoic acid, 3-phenylpropionic acid, 2-ethylhexanoic acid, trimethylacetic acid, 2-phenylpropionic acid, bezoic acid, p-toluic acid, p-anisic acid, 10-undecenoic acid, and the like. Among these, octanoic acid, 3-phenylpropionic acid, 2-ethylhexanoic acid and the like are preferably synthesized.

In the process of the present invention, after the completion of the above reaction, an objective carboxylic acid can be obtained in high yields with a high selectivity by concentrating the resulting mixed solution containing the carboxylic acid and then separating and purifying it by a usual process, such as recrystallization, distillation or sublimation. Moreover, the separation of the catalyst is easily achieved by filtration of the reaction liquid or an operation similar thereto such as decantation and the recovered catalyst can be repeatedly used by washing with water without further purification.

EXAMPLES

The present invention will be explained more specifically with reference to the following Examples, but the present invention is by no means limited by these Examples.

Example 1

Nafion NR50 (500 mg), 30% aqueous hydrogen peroxide solution (1.3 mL, 11 mmol), and octyl aldehyde (1.6 mL, 10 mmol) were mixed and stirred at 90° C. for 2 hours. After the reaction solution was cooled to room temperature, the yield of octanoic acid by measurement of GLC was 93%.

Example 2

Nafion NR50 (500 mg), 30% aqueous hydrogen peroxide solution (1.3 mL, 11 mmol), and octyl aldehyde (1.6 mL, 10 mmol) were mixed and stirred at 90° C. for 2 hours. After the reaction solution was cooled to room temperature, the yield of octanoic acid by measurement of GLC was 93%. The Nafion NR50 was separated from the reaction solution by filtration and washed with 5 mL of water for five times. Then, octyl aldehyde (1.6 mL, 10 mmol) and a 30% aqueous hydrogen peroxide solution (1.3 mL, 11 mmol) were added, followed by stirring at 90° C. for 2 hours. After the reaction solution was cooled to room temperature, the yield of octanoic acid by measurement of GLC was 92%.

Comparative Example 1

Dioxane (10 mL) was used as a solvent so that octyl aldehyde (1.6 mL, 10 mmol) and 30% aqueous hydrogen peroxide solution (1.3 mL, 11 mmol) formed a homogeneous phase, followed by stirring at 90° C. for 2 hours without using any catalyst. After the reaction solution was cooled to room temperature, the yield of octanoic acid by measurement of GLC was 30%.

Comparative Example 2

As a result of carrying out the reaction in the same conditions with Example 1 except that dioxane (10 mL) was added beforehand so that octyl aldehyde and the aqueous hydrogen peroxide solution formed a homogeneous phase, the yield of octanoic acid was 49%.

Example 3

Nafion NR50 (500 mg), 30% aqueous hydrogen peroxide solution (1.3 mL, 11 mmol), and 3-phenylpropionaldehyde (1.3 mL, 10 mmol) were mixed and stirred at 90° C. for 2 hours. After the reaction solution was cooled to room temperature, the yield of 3-phenylpropionic acid by measurement of GLC was 92%.

Example 4

Nafion NR50 (500 mg), 30% aqueous hydrogen peroxide solution (1.3 mL, 11 mmol), and 2-ethylhexyl aldehyde (1.6 mL, 10 mmol) were mixed and stirred at 90° C. for 2 hours. After the reaction solution was cooled to room temperature, the yield of 2-ethylhexanoic acid by measurement of GLC was 65%.

Example 5

Nafion NR50 (500 mg), 30% aqueous hydrogen peroxide solution (1.3 mL, 11 mmol), and trimethylacetaldehyde (1.1 mL, 10 mmol) were mixed and stirred at 90° C. for 2 hours. After the reaction solution was cooled to room temperature, the yield of trimethylacetic acid by measurement of GLC was 32%.

Example 6

Nafion NR50 (500 mg), 30% aqueous hydrogen peroxide solution (1.3 mL, 11 mmol), and 2-phenylpropionaldehyde (1.3 mL, 10 mmol) were mixed and stirred at 90° C. for 2 hours. After the reaction solution was cooled to room temperature, the yield of 2-phenylpropionic acid by measurement of GLC was 10%.

Example 7

Nafion NR50 (500 mg), 30% aqueous hydrogen peroxide solution (1.3 mL, 11 mmol), and benzaldehyde (1.0 mL, 10 mmol) were mixed and stirred at 90° C. for 2 hours. After the reaction solution was cooled to room temperature, the yield of benzoic acid by measurement of GLC was 82%.

Example 8

Nafion NR50 (500 mg), 30% aqueous hydrogen peroxide solution (1.3 mL, 11 mmol), and p-tolualdehyde (1.6 mL, 10 mmol) were mixed and stirred at 90° C. for 2 hours. After the reaction solution was cooled to room temperature, the yield of p-toluic acid by measurement of GLC was 42%.

Example 9

Nafion NR50 (500 mg), 30% aqueous hydrogen peroxide solution (1.3 mL, 11 mmol), and p-anisaldehyde (1.2 mL, 10 mmol) were mixed and stirred at 90° C. for 2 hours. After the reaction solution was cooled to room temperature, the yield of p-anisic acid by measurement of GLC was 4%.

Example 10

Nafion NR50 (500 mg), 30% aqueous hydrogen peroxide solution (1.3 mL, 11 mmol), and 10-undecenaldehyde (2.1 mL, 10 mmol) were mixed and stirred at 90° C. for 2 hours. After the reaction solution was cooled to room temperature, the yield of 10-undecenoic acid by measurement of GLC was 90%.

INDUSTRIAL APPLICABILITY

According to the production process of the present invention, useful carboxylic acids to be widely used as intermediate for various organic compounds can be obtained under mild conditions and in high yields. Moreover, since the process of the present invention does not use any organic solvent, acid, and base, the reaction operations are simple and the operation for solvent removal after the completion of the reaction is not required as well as the recovery and reuse of the catalyst are possible, the influences and toxicity on the environment and a human body are very little, and the process also has an effect of reducing a burden on the environment, so that carboxylic acids can be obtained safely, simply, and efficiently.

The invention claimed is:

1. A process for producing carboxylic acid, which comprises reacting aldehyde-containing oily solution with an aqueous hydrogen peroxide solution in the presence of a catalyst comprising a polymer compound having a sulfonic acid group in a side chain thereof in a heterogeneous solution system.

2. The process for producing carboxylic acid according to claim 1, wherein the polymer compound is at least one polymer selected from a styrene polymer, a copolymer of styrene and divinylbenzene, and a fluorocarbon polymer.

3. The process for producing carboxylic acid according to claim 1, wherein the aldehyde is a compound represented by the following formula (1):

$$RCHO \qquad (1)$$

wherein R represents a monovalent group selected from hydrogen, an alkyl group, a cycloalkyl group, an aryl group, and an aralkyl group.

* * * * *